(12) United States Patent
Naumann

(10) Patent No.: US 6,776,991 B2
(45) Date of Patent: Aug. 17, 2004

(54) METHODS FOR TREATING PRIAPISM

(75) Inventor: Markus K. Naumann, Kurnach (DE)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 10/183,221

(22) Filed: Jun. 26, 2002

(65) Prior Publication Data

US 2004/0001865 A1 Jan. 1, 2004

(51) Int. Cl.$^7$ ............................................. A61K 39/05
(52) U.S. Cl. .................... 424/239.1; 424/94.5; 424/581; 128/898; 222/327; 604/232; 604/204; 604/890.1; 604/19; 604/507; 604/511
(58) Field of Search ................................ 604/232, 204, 604/890.1, 19, 507, 511, 201, 244; 222/327; 128/898; 424/239.1, 581, 94.5, 423, 422, 426, 284.1, 236.1, 94.1, 94.2, 94.67, 542, 600, 682; 514/14, 559, 906, 962, 968; 435/170, 252.1, 822

(56) References Cited

U.S. PATENT DOCUMENTS

| | | | | |
|---|---|---|---|---|
| 4,338,300 A | * | 7/1982 | Gelbard ........................ | 424/94 |
| 5,437,291 A | | 8/1995 | Pasricha et al. | |
| 5,439,938 A | | 8/1995 | Snyder et al. | |
| 5,562,899 A | * | 10/1996 | Gerber ........................ | 424/94.1 |
| 5,562,907 A | * | 10/1996 | Arnon ........................ | 424/236.1 |
| 5,674,205 A | | 10/1997 | Pasricha et al. | |
| 5,766,605 A | * | 6/1998 | Sanders et al. .......... | 424/239.1 |
| 6,063,768 A | | 5/2000 | First | |
| 6,312,708 B1 | | 11/2001 | Donovan | |
| 6,365,164 B1 | * | 4/2002 | Schmidt et al. .......... | 424/239.1 |
| 6,376,460 B2 | * | 4/2002 | Llewellyn-Smith ............ | 514/2 |
| 6,383,509 B1 | | 5/2002 | Donovan et al. | |
| 6,548,544 B1 | * | 4/2003 | Adaikan et al. ............ | 514/559 |

FOREIGN PATENT DOCUMENTS

| | | | | |
|---|---|---|---|---|
| EP | 0 605 501 B1 | | 4/1999 | |
| WO | WO 95/17904 | | 7/1995 | |
| WO | 95/17904 | * | 7/1995 | .......... A61K/38/16 |

OTHER PUBLICATIONS

Aoyagi, T et al, Bulletin of Tokyo Dental College, Nov. 1999, vol. 40(4), pp. 215–217, Sildenafil induced priapism (abstract only).*

Hoogerwerf, WA et al, Gastrointestinal Endoscopy Clinics of North America, vol. 11(2), pp. 311–323, 2001, Pharmacologic therapy in treating achalasia (abstract only).*

Dyksrta, DD et al, Archives of Physical and Medical Rehabilitation, Jan. 1990, apges. 24–26, vol. 71.*

Jenzer, G et al, Neurology, vol. 25, pp. 150–153, Feb. 1975.*

Papadonikolakis, A.S., et al., Transient erectile dysfunction associated with intramuscular injection of botulinum toxin type A, *J. South Orthop Assoc 2002*, May;11(2):116–118.

Teixeira, C.E., et al., "Nonadrenergic noncholinergic relaxation of human isolated corpus cavernosum induced scorpion venom", *Urology*, vol. 57, No. 4, Apr. 2001, pp. 816–820.

Brodie–Meijer, C.C.E., et al., *Nefazodone–induced clitoral priapism*, International Clinical Psychopharmacology 1999 14:257–258.

Compton, M.T., et al., *Priapism Associated with Conventional and Atypical Antipsychotic Medications: a review*, J. Clin Psychiatry 62:5 May 2001 pp. 362–366.

Dykstra, D.D., et al., *Treatment of Detrusor–Sphincter Dyssynergia with Botulinum A Toxin: a double–blind study*, Arch Phys Med Rehabil vol. 71, Jan. 1990, pp 24–26.

Fauci, A.S., et al., *Harrison's Principles of internal Medicine*, 14$^{th}$ Ed, 1998 McGraw–Hill, p. 2321.

Goddar, H., *Pending Changes of the German Employees Invention Law, the impact on university inventions.*, Les Nouvelles, Jun. 2002, pp. 61–65.

Hoffman, R. , et al., *Transcranial magnetic stimulation and auditory hallucinations in schizophrenia*, The Lancet, vol. 355, Mar. 25, 2000, pp. 1073–1075.

Jenzer, G. , et al., *Autonomic dysfunction in botulism B: a clinical report*, Neurology 25:150–153, Feb. 1975.

Jones, D., *High Performance*, Nature, Aug. 3, 1989, vol. 340, p. 348.

Klinge, E., et al., *Contraction and relaxation of the retractor penis muscle and the penile artery of the bull*, VAMMALA 1974, Vammalan Kirjapaino Oy Finland, Acta Physiologica Scandinavica Suppl. 420.

Kohl, A., et al., *Comparison of the effect of botulinum toxin A (BOTOX®) with the highly–purified neurotoxin (NT 201) in the extensor digitorum brevis muscle test*, Mov Disord 2000; 15(suppl 3); 165.

Lue, T.F., *Erectile Dysfunction*, The New England Journal of Medicine, Drug Therapy, Jun. 15, 2000, pp. 1802–1813.

Marchese Ragona, R., et al., *Management of Parotid Sialocele with Botulinum Toxin*, Laryngoscope 109, Aug. 1999, pp. 1344–1346.

Marjama–Lyons, J., et al., *Tremor–Predominant Parkinson's Disease approaches to Treatment*, Disease Management, Drugs & Aging 2000 Aprl. 16(4) 273–278.

Naumann, M., et al., *Pure Autonomic Dysfunction in Botulism Type B*, Abstract No. 89, Arch. Of Pharmacology, Suppl 2, vol. 365, pp. R31 Jun. 2002.

Naumann, M., et al, *Botulinum toxin type A in the treatment of focal, axillary and palmar hyperhidrosis and other hyperhidrotic conditions*, E. Journal of Neurology 1999, 6 (suppl 4):S111–S115.

(List continued on next page.)

Primary Examiner—Lynette R. F. Smith
Assistant Examiner—Ginny Allen Portner
(74) *Attorney, Agent, or Firm*—Stephen Donovan

(57) ABSTRACT

A method for treating priapism in a mammal by administration of a botulinum toxin.

7 Claims, No Drawings

OTHER PUBLICATIONS

Poulain, B., et al., *Inhibition of transmitter release by botulinum neurotoxin A, Contribution of various fragments to the intoxication process*, Eur. J. Biochem 185, 197–203 (Feb. 1989).

Rochat, M.C., *Priapism: a review*, Theriogenology 56:; 56:713–722.

Schantz, E.J., et al, *Properties and Use of Botulinum Toxin and other Microbial Neurotoxins in Medicine*, Microbiological Reviews, vol. 56, No. 1, Mar. 1992, p. 80–99.

Singh, B.R., *Critical aspects of bacterial protein toxins*, Chp. 4, Natural Toxins II, Plenum Press, NY 1996, pp. 63–84.

Wagner, G, et al., *Pathophysiology and diagnosis of male erectile dysfunction*, BJU International (2001), Suppl 3, 88, pp. 3–10.

Zhou, L., et al., *Expression and purification of the light chain of botulinum neurotoxin A: a single mutation abolishes its cleavage of SNAP–25 and neurotoxicity after reconstitution with the heavy chain*, Biochemistry 1995, 34, pp. 15175–15181.

* cited by examiner

METHODS FOR TREATING PRIAPISM

BACKGROUND

The present invention relates to methods treating priapism. In particular the present invention relates to methods for treating priapism with a neurotoxin.

Priapism

Priapism is a prolonged, persistent (usually for four hours or longer) and often painful penile erection which is not associated with a sexual stimulus. Typically, only the corpora cavernosa of the penis is affected, the corpora spongiosum of the glans penis remaining flaccid. Both low blood flow and high blood flow forms of priapism have been described. Priapism derives its name from Priapus, the son of Aphrodite the ancient Greek goddess of love. Priapus was the Greek god of fertility and is shown in statutes, mosaics and pottery from the period with enormous genitalia and an apparently perpetual erection.

The most common cause of priapism is as a side effect of certain pharmacologicals, such as neuroleptic (i.e. thorazine and chlorpromazine), and high-blood pressure (i.e. prazosin) drugs. Notably, about 42 percent of all sickle-cell adults and 64 percent of all sickle-cell children develop priapism. Priapism also has been observed in association with: use of intracavernosal injections of medications to treat impotence (i.e. papaverine, phentolamine, and prostaglandin E1); leukemia; multiple myeloma; Fabry disease; mycoplasma pneumonia; amyloidosis; carbon monoxide poisoning; malaria; spider bites; citalopram use (a selective serotonin reuptake inhibitor); hydralazine; metoclopramide; omeprazole; hydroxyzine; prazosin (especially when used in patients with renal failure); tamoxifen; testosterone; calcium channel blockers; anticoagulants (both warfarin-induced and during heparin infusions); cocaine; the drug ecstasy; ethanol abuse; androstenedione (for athletic related purposes); marijuana, and; certain cancers which infiltrate the penis and prevent the outflow of blood.

Childhood priapism is known to occur in association with leukemia (white blood cells occluding outflow of blood from the penis), sickle-cell disease, trauma to the penis or to the perineum, and spinal cord injury. Priapism of the clitoris (female priapism) has been rarely described. See e.g. Brodie-Meijer C. C. et al., *Nefazodone-induced clitoral priapism*, Int Clin Psychopharmacol 1999 July;14(4):257–8.

Priapism can occur as a result of a disturbance to the normal regulatory mechanisms that initiate and maintain penile flaccidity. Thus, it is believed that activation of post ganglionic (cholinergic) parasympathetic autonomic nerves can induce erection of the penis, while sympathetic (adrenergic) innervation of the penis induces penile detumescence and terminate erection.

Thus, parasympathetic relaxation of penile smooth muscle (possibly mediated by nitric oxide induced drop in cytosolic calcium) causes an erection by permitting blood to flow into penile structures and increase penile cavernosal pressure. Contraction of sympathetic (adrenergic) innervated, penile smooth muscle results in detumescence (a flaccid penis) due to increased drainage from the penis via venous outflow channels, thereby decreasing intracavernosal pressure. Compton M. T. et al., *Priapism associated with conventional and atypical medications: a review*, J Clin Psychiatry 2001;62:362–366; Rochat M. C., *Priapism: a review*. Theriogenology 2001;56:713–722; Wagner G. et al., *Pathophysiology and diagnosis of male erectile dysfunction*, BJU International (2001), 88 (Suppl. 3), 3–10; Lue T F. Erectile Dysfunction. New Engl J Med 2001;342:1802–1813.

Priapism with an onset within 4–6 hours can sometimes be treated successfully with a decongestant (i.e. pseudoephedrine or terbutaline) which acts to decrease blood flow to the penis. If the erection is non-responsive, aspiration can be used to remove about 50 to 150 cc of blood out of the penis through a small needle placed directly in the corporal body, thereby allowing detumesce.

If the erection reoccurs, certain vaso-active type drugs including epinephrine may be instilled into the penis, causing the blood vessels to constrict and prevent the priapism. If this is unsuccessful an alpha-adrenergic agonist (e.g. metaraminol bitartrate, phenylephrine, metaraminol) can be tried, Alpha agonists counteract penile smooth muscle relaxation which causes an erection. However, it is known that an alpha-agonist can cause significant systemic hypertension as well as ventricular tachycardia. Another treatment option is a shunting procedure to permit blood to drain from the engorged penis.

Unfortunately, current therapies for priapism, including drugs, aspiration and shunting, have significant drawbacks and disadvantages, including recurrence of the priapism; bleeding from the holes placed in the penis as a part of a shunt procedure; post-surgical infections including infection of the corporal body and infection of the skin around the corporal body; necrosis of the penis; damage to the urethra; holes between the urethra and the skin; loss of the penis, and death.

Loss of the penis can occur due to post surgical infection or because of penile necrosis due to the duration of the priapism before an effective treatment was initiated. Priapism has resulted in death from suicide as well as from a blood clot formed in the penis after a shunting procedure breaking off and causing pulmonary embolism.

Botulinum Toxin

The anaerobic, gram positive bacterium Clostridium botulinum produces a potent polypeptide neurotoxin, botulinum toxin, which causes a neuroparalytic illness in humans and animals referred to as botulism. Clostridium botulinum and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and poison peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a botulinum toxin (purified neurotoxin complex) type A from the Hall strain of a Clostridium botulinum is a $LD_{50}$ in mice. Interestingly, on a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18–20 grams each.

In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. In 2000 the FDA approved commercial preparations of type A and type B botulinum toxin serotypes for the treatment of cervical dystonia, and in 2002 the FDA approved a type A botulinum toxin for the cosmetic treatment of certain hyperkinetic (glabellar) facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, Hc, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by Clostridium botulinum bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56: 80–99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of $3 \times 10^7$ LD$_{50}$ U/mg or greater. This known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD$_{50}$ U/mg or greater; purified botulinum toxin type B with an approximately 156 kD molecular weight with a specific potency of $1-2 \times 10^8$ LD$_{50}$ U/mg or greater, and; purified botulinum toxin type F with an approximately 155 kD molecular weight with a specific potency of $1-2 \times 10^7$ LD$_{50}$ U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

It has been reported that a botulinum toxin has been used in clinical settings as follows:

(1) about 75–125 units of BOTOX®[1] per intramuscular injection (multiple muscles) to treat cervical dystonia;

[1] Available from Allergan, Inc., of Irvine, Calif. under the tradename BOTOX®.

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4);273–278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January;71:24–6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as hypersalivation and rhinittis, with a botulinum toxin.

Furthermore, various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

Erectile dysfunction has been reported as a symptom of botulism. Jenzer G., et al., *Autonomic dysfunction in botulism B: a clinical report*, Neurology 1975;25:150–153; Naumann M. et al., *Pure autonomic dysfunction in botulism type B*, Naunyn Schmiedeberg's Archives of Pharmacology June 2002 (supp 2); 365 (abstract 89 at R31). This may be a result of circulating botulinum toxin present in a patient with botulism acting to block release of acetylcholine from cholinergic parasympathetic nerve endings in the corpora cavernosa of the penis. This would cause an inhibition of penile smooth muscle relaxation and therefore a reduced flow of blood into penile structures, and hence a flaccid penis. Contrarily, it has been speculated that a botulinum toxin can be used to cause an erection of the penis. Jones D. *High performance*. Nature 1989;3:348.

It is known that botulinum toxin type A can have an efficacy for up to 12 months (*European J Neurology* 6 (Supp 4): S111–S1150:1999), and in some circumstances for as long as 27 months. *The Laryngoscope* 109:1344–1346:1999. However, the usual duration of an intramuscular injection of Botox® is typically about 3 to 4 months.

The success of botulinum toxin type A to treat a variety of clinical conditions has led to interest in other botulinum toxin serotypes. Additionally, pure botulinum toxin has been used to treat humans. see e.g. Kohl A., et al., *Comparison of the effect of botulinum toxin A (Botox (R)) with the highly-purified neurotoxin (NT 201) in the extensor digitorum brevis muscle test*, Mov Disord 2000;15(Suppl 3):165. Hence, a pharmaceutical composition can be prepared using a pure botulinum toxin.

The botulinum toxin molecule (about 150 kDa), as well as the botulinum toxin complexes (about 300–900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

A commercially available botulinum toxin containing pharmaceutical composition is sold under the trademark BOTOX® (available from Allergan, Inc., of Irvine, Calif.). BOTOX® consists of a purified botulinum toxin type A complex, albumin, and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of Clostridium botulinum toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative; 0.9% Sodium Chloride injection is used by drawing up the proper amount of diluent in the appropriate size syringe. Since BOTOX® is denatured by bubbling or similar violent agitation, the diluent is gently injected into the vial. BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C. BOTOX® is administered within four hours after the vial is removed from the freezer and reconstituted. During these four hours, reconstituted BOTOX® can be stored in a refrigerator (20 to 8° C.).

Other commercially available botulinum toxin containing pharmaceutical compositions include Dysport® (Clostridium botulinum type A toxin haemagglutinin complex with albumin and lactose in the formulation, available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

Acetylcholine

Typically, only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances, acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is an effective and long lasting treatment of priapism with few if any side effects.

SUMMARY

The present invention meets this need and provides an effective and long lasting treatment of priapism with few if any side effects Definitions As used herein, the words or terms set forth below have the following definitions.

"About" means that the item, parameter or term so qualified encompasses a range of plus or minus ten percent above and below the value of the stated item, parameter or term.

"Biological activity" with regard to a neurotoxin includes an ability of the neurotoxin to reduce or inhibit presynaptic release of acetylcholine.

"Local administration" means direct administration by a non-systemic route at or in the vicinity of the site of an affliction or disorder.

Thus, local administration of a pharmaceutical excludes, for example, intravenous or oral administration, but includes, for example, intramuscular or subcutaneous injection or implant placement drug administration. Systemic administration of a botulinum toxin is contraindicated because botulism can result.

"Neurotoxin" includes Clostridial neuro toxins both in pure toxin and as complexed with one to more non-toxin, toxin associated proteins, whether made by the native Clostridial bacterium or by recombinant means in a non-Clostridial species.

"Purified or pure botulinum toxin" means a botulinum toxin that is isolated, or substantially isolated, from other proteins, including proteins that form a botulinum toxin complex. A purified botulinum toxin may be greater than 95% pure, and preferably is greater than 99% pure.

"Patient" means a human or non-human subject receiving medical or veterinary care.

The present invention encompasses a method for treating priapism by local administration of a Clostridial toxin to a mammal with priapism. The Clostridial toxin can be a botulinum toxin, such as a botulinum toxin type A, B, C, D, E, F or G. Preferably, the botulinum toxin is a botulinum toxin type A.

The botulinum toxin can be administered in an amount between about 1 unit and about 10,000 units and the priapism can be substantially alleviated for between about 2 weeks and about 6 months. Thus, for example, about 1 unit of a type A toxin can be to treat clitoral priapism or infantile priapism. About 10,000 units of a type B botulinum toxin can be used to treat a large mammal with a penis of considerable size. Notably, the local administration step is carried out by direct administration of the Clostridial toxin to a penis of the mammal.

A further embodiment of the present invention is a method for treating priapism, by local administration of a botulinum toxin to a penis of a mammal with priapism. A most preferred embodiment of the present invention is a method for treating priapism, the method comprising the step of local administration of a botulinum toxin type A to a penis of a mammal with priapism.

DESCRIPTION

My invention is based upon the discovery that long term alleviation of priapism can be achieved by local administration of a neurotoxin to a mammal afflicted with this condition.

The mammal treated can be a human or another species which exhibits priapism, such as a domesticated mammal, such as a dog or a horse. See e.g. Rochat M. C., *Priapism: a review*. Theriogenology 2001;56:713–722.

My invention encompasses use of a neurotoxin, such as a Clostridial toxin, such as a botulinum toxin (any of the serotypes A, B, C, D, E, F or G) for the therapeutic treatment of priapism in humans or other mammals. A method within the scope of my invention can be practiced by local administration of a of botulinum toxin to treat a persistent erection of the penis, i.e. priapism.

To reiterate, an embodiment of the present invention can be carried out by injecting a botulinum toxin type into a penis of the mammal to be treated. As set forth above, it is believed that cholinergic parasympathetic innervation induces penile erection of the penis, while sympathetic nerves induce penile detumescence (flaccidity). Without wishing to be bound by theory, it can be hypothesized that a botulinum toxin, by inhibiting release of acetylcholine from cholinergic parasympathetic nerve endings in the corpora cavernosa of the penis, causes an inhibition of penile smooth muscle relaxation. Hence, the unaffected adrenergic sympathetic innervation causes penile smooth muscle contraction and thereby a flaccid penis because of reduced blood inflow to penile structures. Thus, the treatable priapism within the scope of the present invention is a priapism responsive to a downregulation of penile parasympathetic innervation. High flow priapism may be unsuitable for treatment according to the present invention. For example, a patient who suffers injury to the perineum can exhibit traumatic high-flow priapism because a genital artery had ruptured. The blood enters the artery, goes into the corporal body of the penis, thereby creating an erection, and then immediately leaves the penis because the penile veins were not constricted. A continuous (i.e. high flow) of blood form the ruptured artery into the penis maintains the erection. With such a patient an arteriogram of the pudendal arterial system can be carried out to identify the point of the fistula and a small coil of material (a stent) placed into the damaged artery. Injection of a botulinum toxin would probably have been ineffective to treat such a high flow priapism.

Preferably, because of its ready availability and clinical history to successfully treat a number of indications, a method within the scope of the present invention includes local administration of a botulinum type A. A botulinum toxin type B can also be used because a botulinum toxin type B is also commercially available, although it is used with a larger protein load, as compared to type A toxin. A botulinum toxin type A used in a method within the scope of the present invention can be a complex of toxin and non-toxin proteins, which together comprise a total molecular weight of about 900 kiloDaltons and which is used at a dose of between 1 and 100 units per patient, the range being based upon size, age and health of the patient, as well as upon the particular commercial preparation of the type A botulinum toxin used. A botulinum toxin type B used in a method within the scope of the present invention can be a pure toxin or complex of toxin and non-toxin proteins, which together comprise a total molecular weight of about 700 kiloDaltons and which is used at a dose of between about 50 and about 20,000 units per patient treated.

Other botulinum toxin serotypes can be used in proportion to the dosages and concentrations exemplified herein, according to their respective levels of biological activity. The present invention also encompasses methods for concurrent or serial administration of a mixture of two or more of the above neurotoxins to effectively treat a patient with priapism.

A neurotoxin, such as a botulinum toxin can require, according to the methods of the present invention, from about 1 hour to 7 days to achieve it's desired detumescence effect.

Additionally a neurotoxin, such as a botulinum toxin, according to the present invention is always locally administered in vivo directly to the patient's (a mammal) penis. Known local drug administration methods suitable for this purpose include a syringe for liquid pharmaceutical injection and insertion of a controlled release implant (See e.g. U.S. Pat. Nos. 6,383,509 and 6,312,708 (Donovan)). Systemic routes of drug administration such as oral or intravenous administration are excluded from the scope of the present invention because systemic distribution of a neurotoxin, such as a botulinum toxin, is not desirable.

In another embodiment, the methods comprise the administration of a neurotoxin, for example a Clostridial neurotoxin, to a patient wherein the neurotoxin differs from a naturally occurring (native) neurotoxin by at least one amino acid. For example, variants of botulinum toxin type A as disclosed in *Biochemistry* 34;5175–15181:1995 and *Eur. J. Biochem,* 185;197–203:1989 can be administered. Practice of the present invention can provide a priapism treatment effective for between 2 weeks (i.e. if a type E toxin is used) to up to about 6 months or longer (type A toxin is used).

The amount of the neurotoxin, such as a botulinum toxin, administered can vary widely according to the particular disorder being treated, its severity and other various patient variables including size, weight, age, and responsiveness to therapy. Generally, the dose of neurotoxin to be administered will vary with the age, presenting condition and weight of the mammal to be treated. The potency of the neurotoxin to be administered is also a consideration.

In one embodiment according to this invention, the therapeutically effective doses of a neurotoxin, for example a botulinum toxin type A complex (as Botox), can be between about 1 unit and about 500 units Less than about 1 unit can result in a suboptimal detumescence effect while more than about than about 500 units of a type A preparation can result in undesired systemic effects.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill). For example, the route and dosage for administration of a neurotoxin according to the present disclosed invention can be selected based upon criteria such as the solubility characteristics of the neurotoxin chosen as well as the age and health of the patient.

A suitable neurotoxin can be obtained by culturing an appropriate bacterial species. For example, botulinum toxins can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture.

If a modified neurotoxin is to be used according to this invention, recombinant techniques can be used to produce the desired neurotoxins. The technique includes steps of obtaining genetic materials from natural sources, or synthetic sources, which have codes for a neuronal binding moiety, an amino acid sequence effective to translocate the neurotoxin or a part thereof, and an amino acid sequence having therapeutic activity when released into a cytoplasm of a target cell, preferably a neuron.

A method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

Example 1

Treatment of Priapism with Botulinum Toxin Type A

A 24 year old male presents with an erection of two days duration. Examination reveals a hard penis with a soft glans.

The rectum and abdomen exhibit no evidence of cancer. A complete blood count (CBC, coagulation profile, platelet count and urinalysis does not indicate leukemia or sickle cell disease.

A penile nerve block is carried out by injecting 1% lidocaine around the base of the penile shaft. A botulinum toxin is then injected percutaneously into both corpora cavernosa of the penis at multiple sites. This allows a wide diffusion of the botulinum toxin within the corpus cavernosum. The botulinum toxin injections can be performed with a very thin needle (30 G or smaller) for patient comfort. The botulinum toxin is injected at about 4–8 sites along each corpus cavernosum. Preferably, both corpora cavernosa of the penis are injected. The dose per corpus cavernosum is 20–40 units of a botulinum toxin type A (i.e. Botox®) (distributed at 4–8 sites). A bilateral injection requires 40–80 units in total. The volume to be injected has to be low and should not exceed 0.5 ml per corpus cavernosum. Alternately, about four times these unit amounts of an alternate botulinum toxin type A (i.e. 160–320 total units of Dysport®) can be used or about 50 times the given unit amounts if a botulinum toxin type B (i.e. 1000–2000 total units of MyoBloc™). The effect of botulinum toxin can occur within the first 24 hours after injection and consists of a penile detumescence and termination of erection. Duration of effect is 2–6 months.

Example 2

Treatment of Priapism with Botulinum Toxin Type B

D. E. was a medical professional who had read about the treatment of erectile dysfunction with penile injections. He injected himself with a dose that far exceeded what he needed and developed a rock-hard penis which he enjoyed for several hours, after which the condition became painful and he presented himself at a hospital emergency room. The procedure set forth in Example 1 was followed except that the dose per corpus cavernosum is 1000–4000 units of a botulinum toxin type B (i.e. MyoBloc™) (distributed at 4–8 sites). A bilateral injection requires 2000–8000 units in total. The effect of botulinum toxin type B can occur within the first 24 hours after injection and consists of a penile detumescence and termination of erection. Duration of the effect is 2–6 months.

Example 3

Treatment of Priapism with Botulinum Toxin Type C–G

A 42 year old male receiving neuroleptics for psychiatric disorders presents with an erection of 14 hours duration. A botulinum toxin type C, D, E, F or G is injected percutaneously into both corpora cavernosa of the penis at multiple sites. This allows a wide diffusion of the toxin within the corpus cavernosum. The botulinum toxin injections can be performed with a very thin needle (30 G or smaller). The toxin is injected at about 4–8 sites along each corpus cavernosum. Preferably, both corpora cavernosa of the penis are injected. The dose per corpus cavernosum and the duration of the detumescence is dependent upon the serotype of the botulinum toxin used. The botulinum toxin selected is injected at 4–8 sites bilaterally. The effect of botulinum toxin can occur within about 2 hours after injection and can last up to six months.

Example 4

Treatment of Equine Priapism with a Botulinum Toxin

A four year old thoroughbred stallion is examined for priapism which developed subsequent to use of a phenothiazine-derivative tranquilizer. The stallion is unresponsive to either lavage of the corpus cavernosum penis with heparinized 0.9% NaCl solution or intravenous benztropine mesylate.

Three days after onset of priapism, the penis is firm and noncompliant, and penile pain sensation and ability to retract the penis are lost. Ultrasonography confirmed thrombosis of the corpus cavernosum penis. 20 units of Botulinum toxin type A (Botox®) are injected at 2 sites along each corpus cavernosum (80 units total). The erection subsides, the penis retracts into the sheath and the stallion is able to subsequently achieve normal erections.

A method according to the invention disclosed herein has many advantages, including the following:
1. effective relief of priapism can be quickly achieved.
2. long term relief of priapism can be achieved.
3. there are no or minimal side effects form the practice of the disclosed invention.

Various publications and/or references have been cited herein, the contents of which, in their entireties, are incorporated herein by reference.

Although the present invention has been described in detail with regard to certain preferred methods, other embodiments, versions, and modifications within the scope of the present invention are possible. For example, besides a botulinum toxin, other neurotoxins which can accomplish the same desired result (treatment of priapism by local administration of the toxin) are within the scope of my invention. Thus, a tetanus toxin can show efficacy as well as recombinant, chimeric and modified Clostridial toxins, including recombinant, chimeric and modified botulinum toxins. Additionally, the present invention includes a treatment of priapism by local administration of two or more neurotoxins, such as two or more botulinum toxins, are administered concurrently or consecutively. For example, botulinum toxin type A can be administered until a loss of clinical response or neutralizing antibodies develop, followed by administration of botulinum toxin type B or E. Alternately, a combination of any two or more of the botulinum serotypes A–G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect. Finally, my invention encompasses use of a relatively short acting botulinum toxin, such as a botulinum toxin type E, where use of a short acting toxin is indicated.

The present invention also includes use of a medicament comprising a Clostridial toxin, such as a botulinum toxin for treating priapism by local administration of the Clostridial toxin.

Accordingly, the spirit and scope of the following claims should not be limited to the descriptions of the preferred embodiments set forth above.

I claim:

1. A method for treating priapism, the method comprising the step of locally administering to the penis of a mammal with priapism a botulinum toxin in an amount effective to treat priapism wherein the botulinum toxin is selected from the group consisting of botulinum toxin types A, B, C, D, E, F and G.

2. The method of claim 1, wherein the botulinum toxin is a botulinum toxin type A and the botulinum toxin type A is administered in an amount between 1 unit and about 500 units.

3. The method of claim 1, wherein the botulinum toxin is a botulinum toxin type B and the botulinum toxin type B is administered in an amount between 1 unit and about 10,000 units.

4. The method of claim 1, wherein the priapism is substantially alleviated for between about 2 weeks and about 6 months.

5. The method of claim 1, wherein the botulinum toxin in administered to the corpus cavernosum of the penis.

6. A method for treating priapism, the method comprising the step of locally administering to the penis of a mammal with priapism a botulinum toxin type A effective to treat priapism.

7. The method of claim 6, wherein the botulinum toxin type A is administered in an amount between 1 unit and about 500 units.

* * * * *